(12) United States Patent
Smith et al.

(10) Patent No.: US 6,241,651 B1
(45) Date of Patent: Jun. 5, 2001

(54) MINIATURIZED SOURCE OF IONIZING RADIATION AND METHOD OF DELIVERING SAME

(75) Inventors: Leif Smith; Carolina Ribbing, both of Uppsala (SE)

(73) Assignee: Radi Medical Technologies AB, Uppsala (SE)

( * ) Notice: Subject to any disclaimer, the term of this patent is extended or adjusted under 35 U.S.C. 154(b) by 0 days.

(21) Appl. No.: 09/379,782

(22) Filed: Aug. 24, 1999

Related U.S. Application Data

(63) Continuation of application No. PCT/SE98/00348, filed on Feb. 25, 1998, and a continuation-in-part of application No. 08/805,296, filed on Feb. 25, 1997, now Pat. No. 5,984,853.

(51) Int. Cl.[7] .................................................... A61N 5/00
(52) U.S. Cl. .................................................................. 600/1
(58) Field of Search ............................ 600/1–8, 407, 600/427; 378/64, 65, 108, 116, 62, 119, 121, 145, 137, 138, 110, 112

(56) References Cited

U.S. PATENT DOCUMENTS

| | | | |
|---|---|---|---|
| 5,090,043 | 2/1992 | Parket et al. ........................ | 378/121 |
| 5,442,678 | 8/1995 | Dinsmore et al. .................... | 378/137 |
| 5,452,720 | 9/1995 | Smith et al. .............................. | 600/1 |
| 5,528,652 | 6/1996 | Smith et al. ........................ | 600/427 |
| 5,729,583 | 3/1998 | Tang et al. ............................ | 378/122 |

FOREIGN PATENT DOCUMENTS

| | | |
|---|---|---|
| 0630 038 A1 | 12/1994 | (EP) . |
| WO 97/07740 | 3/1997 | (WO) . |

OTHER PUBLICATIONS

Brodie, "Vacuum Microelectronic Devices", Proceedings of the IEEE, vol. 82(7):1006–1034, (1994).

*Primary Examiner*—John P. Lacyk
(74) *Attorney, Agent, or Firm*—Foley & Lardner

(57) ABSTRACT

A method and apparatus of creating a miniaturized source of radiation and delivering radiation to a location such as a therapy location. The radiation source includes a member made of a material emitting electrons when energy is supplied to the member. There is an electron retarding member disposed opposite the electron emitting member, and the electron retarding member is made of a material emitting ionizing radiation when electrons are retarded therein. The radiation source is further provided on an elongated member in a distal region thereof, and the elongated member is insertable into the body.

32 Claims, 7 Drawing Sheets

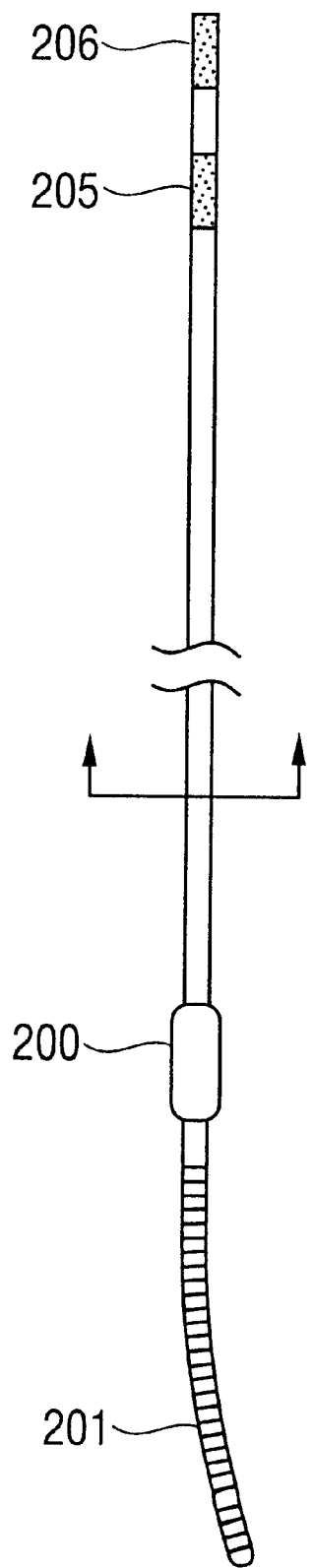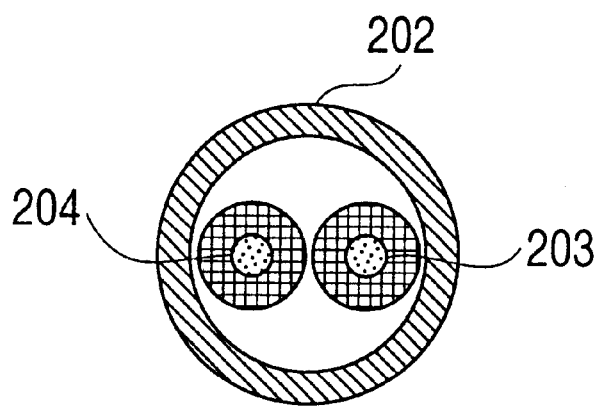

FIG. 9
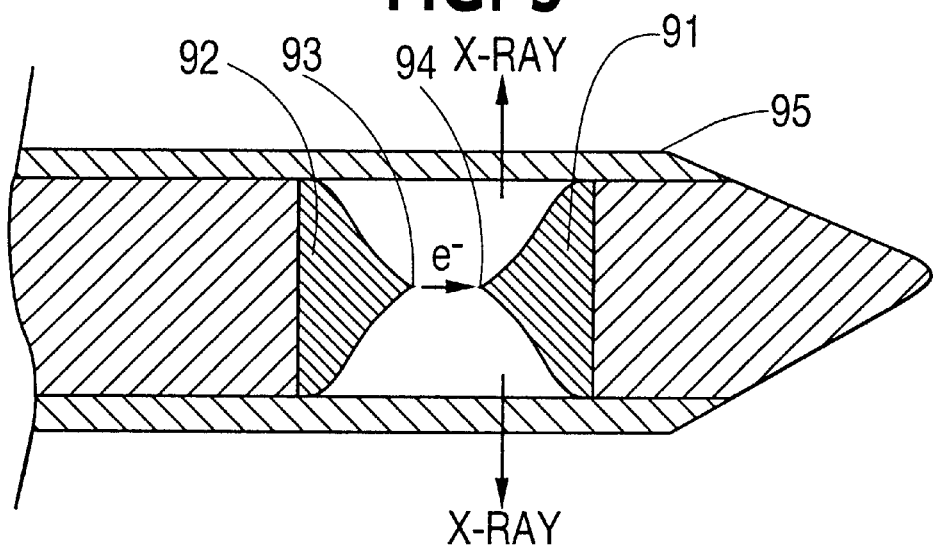
FIG. 10a FIG. 10b FIG. 10c
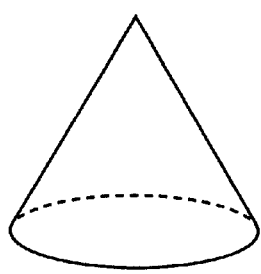 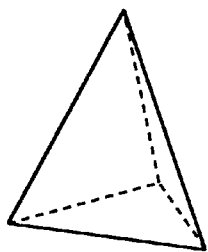 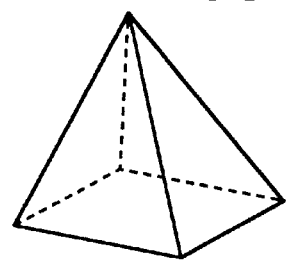
FIG. 11
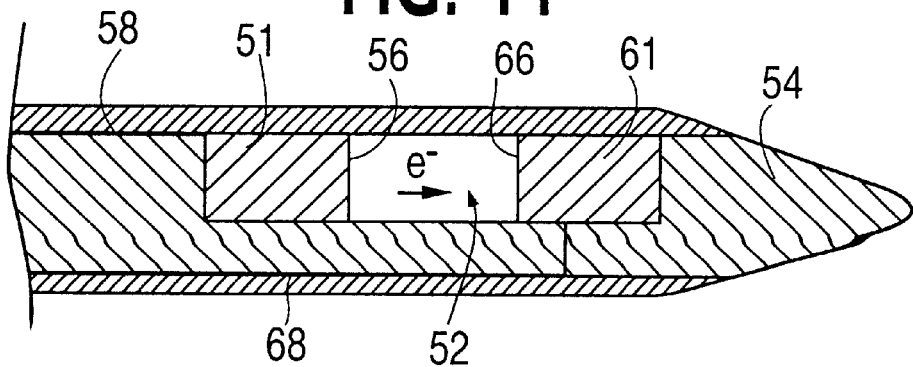

MINIATURIZED SOURCE OF IONIZING RADIATION AND METHOD OF DELIVERING SAME

The Applicants hereby claim the benefit of U.S. application Ser. No. 08/805,296, filed Feb. 25, 1997, and PCT/SE98/00348, filed Feb. 25, 1998 (which designated the United States). This application is a continuation of PCT/SE98/00348, filed Feb. 25, 1998, and a continuation-in-part of U.S. application Ser. No. 08/805,296, filed Feb. 25, 1997, now U.S. Pat. No. 5,984,853. The entire contents (including the claims) of PCT/SE98/00348 (published as WO 98/36796) and Ser. No. 08/805,296 are incorporated herein by reference.

BACKGROUND OF THE INVENTION

1. Field of the Invention

The invention relates to a method and apparatus for the use of radiation sources in therapy, and in particular to a miniaturized radiation source having the capability of being switched on and off at the operator's discretion.

2. Related Art

The manufacture of radiation devices has been under development during the last 30 years. The primary applications for these devices are in microelectronics, diodes and transistors.

However more recently, devices that generate radiation in the visible frequency region have been used for displays of the Flat Panel Display type, and this technology has become a separate research area for applications in the television field, etc. the primary effort has been to decrease the anode to cathode voltage, so that these devices can be used in general purpose electronic circuits. A more detailed description of this research can be found in an article entitled "Vacuum Microelectronic Devices", in *Proceedings of the IEEE,* Vol. 82 no. 7, July 1994.

In this article there is disclosed the principles and basic construction of micro field-emission sources. It is stated therein that it is necessary to have emission areas no larger than $10^{-2}$ cm$^2$ in order to obtain uniform field emission. Therefore, it is necessary to form the emitter in the shape of a needle with a tip having an end radius less than 1 μm. A specific design of the emitter is a metal cone, $10^{-4}$ cm tall with a tip radius of 30 nm. Also, there is disclosed the provision of an accelerating electrode (gate) spaced 60 nm from the tip.

In this application, these field emitting devices, among others, can be utilized to emit ionizing radiation with energies high enough to be used for medical therapy.

Radiation therapy is a well established method for treatment of several serious diseases, including cancer. Either alone or combined with other forms of therapy, the irradiation of human or animal tissue with ionizing radiation has proven to be very effective, and is used throughout the world and at several levels in health care organizations from specialized university clinics to regional and county levels. However, complications and side effects are often present. Ionizing radiation is biologically destructive in the sense that the structure of biomolecules is irreversibly changed, frequently leading to cellular disorganization, functional damage and even death. The result is also no-specific. A common problem is to limit the radiation exposure to areas of disease, in order to avoid destruction of healthy tissue.

Traditional radiation therapy makes use of radioactive nuclei, particle accelerators or high voltage generators in order to create radiation with such a high energy that it penetrates the patient's body. The radiation source is usually located outside the body, and means for collimating the radiation is used to concentrate it on the tissue where therapy is required. A difficult compromise is to maximize the therapeutic dose while minimizing the radiation exposure of healthy tissue.

In recent years, miniaturized radiation sources consisting of radioactive substances contained at the tip of the metal wire have been introduced. With such a localized radiation source it is possible to concentrate the dose, to a small region. However, the use of radioactive substances is impractical for several reasons. First, the source must be properly shielded during introduction into the body in order to avoid exposure of healthy tissue. Second, all handling procedures must be carefully controlled to avoid exposure by mistake. Third, the dose and energy of radiation are not easily controlled.

SUMMARY OF THE INVENTION

The present invention provides an adequate solution to these problems. It has now been ascertained that the principle of field emission and thermionic emission is possible for use in medical procedures, namely for delivering radiation to a therapy location in a living body. One aspect of the invention comprises a miniaturized radiation source which is electronically controllable to generate exactly the required energy or wavelength of radiation. It can be switched on and off as desired. Furthermore, the delivered intensity and dose can be independently controlled, and the source can be manufactured with extremely small dimensions. For certain purposes it will have a volume of less than $10^{-3}$ mm$^3$, whereas for other purposes it may be as large as 1 cm$^3$.

Thus, in one aspect of the invention there is provided an apparatus for delivering radiation to a therapy location in a living body, comprising a miniaturized source of ionizing radiation, the radiation source ionizing radiation, the radiation source comprising a member made of a material emitting electrons when energy is supplied to the member, an electron retarding member disposed opposite the electron emitting member, the electron retarding member being made of a material emitting ionizing radiation when electrons are retarded therein, the radiation source being provided on an elongated member in the distal region thereof, and the elongated member being insertable into the body.

In another aspect of the invention there is provided a method of delivering radiation to a therapy location in a living body.

BRIEF DESCRIPTION OF THE DRAWINGS

The invention will be more fully understood from the following detailed description in conjunction with the drawings, wherein:

FIG. 4a illustrates an embodiment where the radiation source is mounted at the distal end of a guide wire;

FIG. 4b is a cross-section taken along B—B in FIG. 4a;

FIG. 9 illustrates a preferred embodiment of the radiation source according to the invention;

FIG. 10 illustrates alternative electrode shapes suitable for use in the embodiment of FIG. 9;

FIG. 11 illustrates a still further embodiment of the radiation source of the invention;

DETAILED DESCRIPTION OF THE PREFERRED EMBODIMENTS

The basic physical principle behind the radiation source is well known from the literature of modern physics. When high-energy electrons are retarded by nuclei having a large atomic-weight, electromagnetic radiation is emitted. The primary radiation, denoted "bremsstrahlung", has a continuous spectrum with a peak corresponding to given fraction of the electron energy. The emitted radiation can have an energy peak from a few electron volts (eV) to several million electron volts (MeV), depending on the energy of the incident electrons. In terms of wavelength, this corresponds to a range from ultraviolet light (10–4000 A) via X-rays (0.1–100 A) to gamma radiation (<0.10 A). Thus, by varying the energy of the electrons, the wavelength peak can be displaced accordingly. In addition to bremsstrahlung, which basically has a continuous spectrum, absorption or emission peaks corresponding to atomic electron transition may be embedded in the spectrum, depending on the materials contained in the transmission medium.

Figure 1:
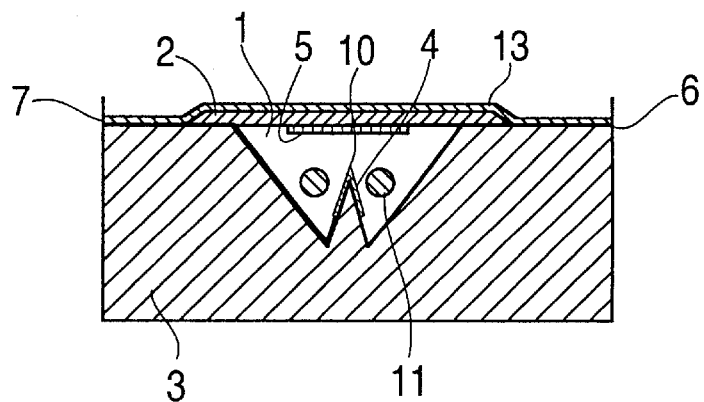
FIG. 1 shows a cross-section of the radiation source according to the invention, wherein the field emission principle is employed.
Figure 2A:
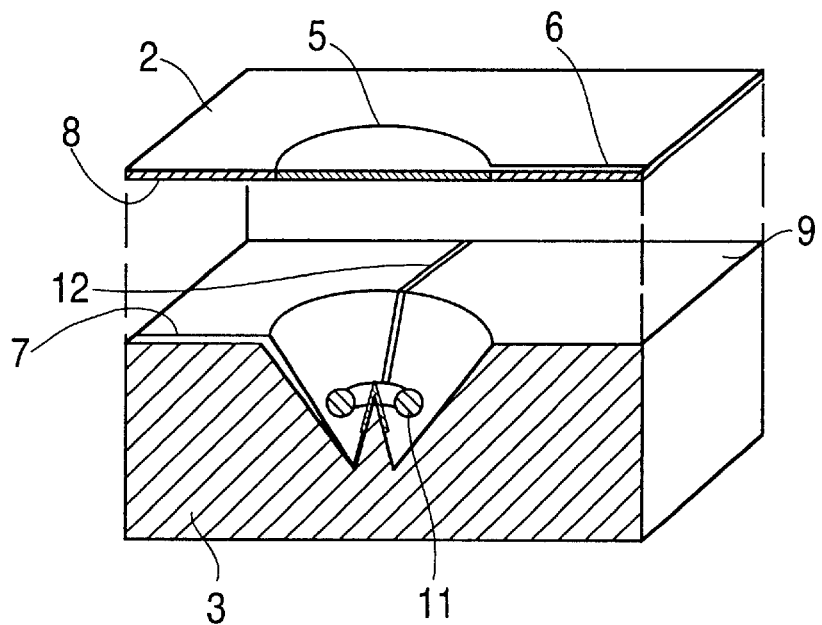
FIG. 2a shows an exploded perspective view of the radiation source according to the invention of FIG. 1.
Figure 2B:
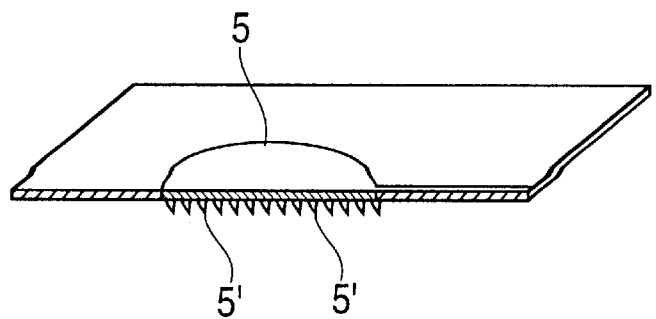
FIG. 2b is a view showing in detail an alternative embodiment of an anode for the device of FIG. 2a, wherein the anode is provided with micro tips.

The details of the radiation source and its function will be described with reference to FIGS. 1 and 2. Basically, the source is built up from two plates 2, 3 with a recessed region forming a microcavity 1 at one or several localities. An anode material 5 and a cathode 4 with extremely small dimensions, and having the form of a sharp tip 10 are located within this microcavity. The radius of curvature of the tip 10 of the cathode is preferably in the nanometer range. If a voltage is applied between the anode 5 and cathode 4, the electric field strength will be extremely high at the cathode. A positive voltage on the anode will cause electrons to be emitted from the cathode by the phenomenon known as field emission. Alternatively, the cathode may be heated to high temperatures, giving rise to thermal emission of electrons. This will be further discussed below with reference to FIG. 6. The electrons are accelerated by the electric field, until they are retarded by the impact at the anode. The anode 5 preferably consists of a metal having a high atomic weight, corresponding to an atomic number exceeding 50. In a preferred embodiment, the anode 5 is made of tungsten which is an endurable metal which can be deposited in the form of thin films either by physical or chemical deposition techniques. Other metals include cobalt, molybdenum and aluminium. The cathode preferably consists of a thin deposited film of a material having a low work function, i.e. the energy required for an electron to be emitted from the surface into the ambient. Materials with this property are oxides of metals from Groups I and II in the periodic table, including cesium, barium and magnesium.

It is also conceivable to design the anode 5 such that it comprises a large number of micro tips 5'. Such micro tips may be formed of diamond particles extending from a base matrix of a conductive material, e.g. a metal. The diamond micro tips may furthermore be coated with e.g. a metal or other conductive material, on order to improve the conductivity thereof. Other materials having properties similar to that of diamond are conceivable, i.e. having similar hardness and conductivity. It is also possible to provide said micro tips by making the anode of or coating it with a polycrystalline material, to obtain a certain surface roughness, thus providing micro tips.

The anode 5 and cathode 4, may be connected to a voltage source by electrically conducting leads 6, 7, which may, at least partly, be an integral part of the plates 2, 3. This can be achieved by deposition of strips by evaporation, sputtering or chemical vapor deposition. Alternatively, if the plates 2, 3 are semiconductors, the leads 6, 7 may be doped regions according to well-known technology. In a preferred embodiment, a third electrode 11 is also present within the microcavity 1. This electrode 11 acts as a gate, controlling the electron current emitted toward the anode 5. The gate electrode has a separate lead 12, enabling a separate voltage source to be connected. According to the well-known theory of vacuum tubes, the anode current is controlled by the gate voltage. This will directly influence the intensity of the emitted radiation which is approximately proportional to the anode current. The emitted dose is simply the time integral of this intensity. By separate and independent control of the gate and anode voltages, it is thus possible to independently control the emitted dose and energy, respectively.

The leads 6, 7 and 12 must be properly isolated to avoid short circuit or current leakage. If the plate materials by themselves are not isolating themselves, passivating films may be necessary to ensure proper isolation. Furthermore, the lateral location of the leads is preferably chosen to minimize the electric field across material barriers. The voltage to the anode and cathode should preferably be in the kV range in order to obtain radiation of sufficient energy.

Figure 6:
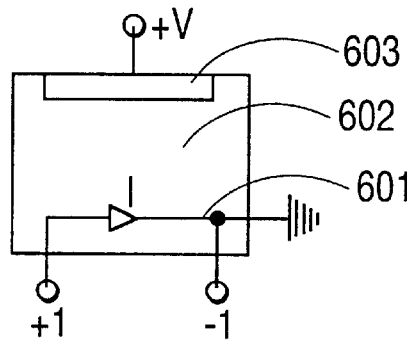
FIG. 6 shows schematically the radiation source according to the invention, wherein the thermionic emission principle is employed.

With reference to FIG. 6, there is schematically shown an implementation wherein the thermionic emission principle is employed. Through a thin wire 601 or filament disposed in a microcavity 602, such as the one disclosed above, a current I is passed. The temperature will be so high that electrons will be emitted and accelerated by an electronic voltage imposed across the filament 601 and an anode 603, also disposed in microcavity 602.

There are two principally different ways of fabricating the radiation source according to the invention. One way is to use two separate solid substrates and define the structures containing the cathode 4, the gate 11, with their leads 7 and 12, and the recess or microcavity 1 in one substrate. The anode 5 and its lead 6 are defined in the second substrates. Lithographic techniques according to well-known art are preferably used in defining these structures. Then finally the two substrates, corresponding to plates 2 and 3, are bonded together, using the technique such as solid-state bonding. If the bonding in performed in a vacuum, the microcavity 1 will remain evacuated, since the bonded seal is almost perfectly hermetic, provided that no organic materials are used. Absolute vacuum is not a necessity, but the density of gas molecules inside the microcavity must not be so high that the accelerating electrons are excessively impeded.

A requirement for successful bonding is that the surfaces 8 and 9 being bonded are flat and smooth with a precision corresponding to a few atomic layers. A second requirement is that all structures are able withstand a relatively high annealing temperature, approximately 600–1000° C., without damage. This first fabrication technique is basically known as bulk micromachining, in contrast to its alternatively, surface micromachining. According to this, all structures are formed by depositions on one single substrate, again using lithography to define the two-dimensional pattern on the surface. The microcavity 1 is formed by first depositing a sacrificial layer which is etched away after the uppermost layers have been deposited. Closing of the microcavity can be done by depositing a top layer, covering openings which are required for the etching of the sacrificial layer.

Both described methods of fabrication are feasible and lead to similar device performance. Indeed, from examining a final device, it may be difficult or even impossible to conclude which fabrication procedure has been used. An important characteristic of the proposed fabrication techniques is that the manufacturing cost per unit becomes very small when the source elements are fabricated in large numbers. This is due to the fact that batch fabrication with thousands of units per batch is feasible.

Figure 3A:
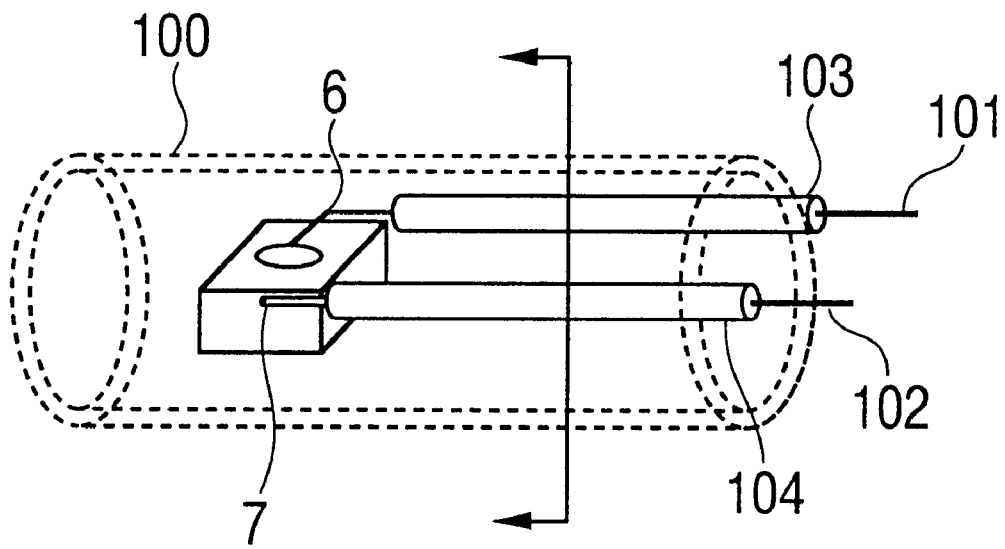
FIG. 3a illustrates an embodiment where the radiation source is mounted in a tube.
Figure 3B:
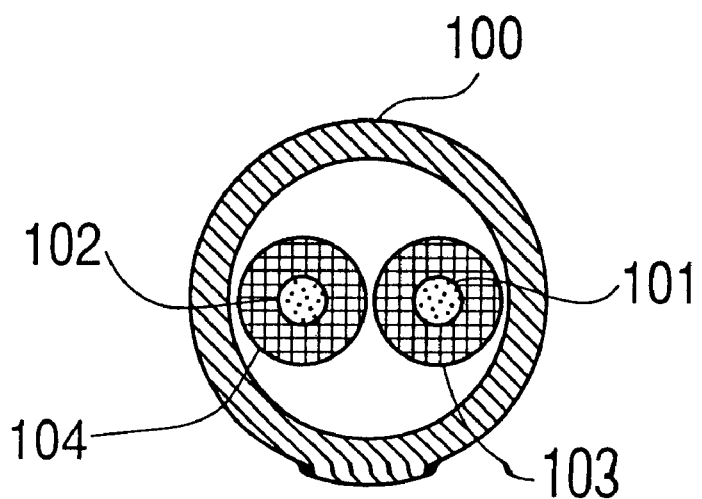
FIG. 3b is a cross-section of the tube of FIG. 3a, taken along B—B.

In FIG. 3 an embodiment is shown where the source and its leads 6, 7 are mounted inside a tubular element, such as a cannula 100, consisting of a material which is transparent to the emitted radiation.

Preferably, the tubular element (or the hollow portion where the source is mounted in the case of a needle), is made from elements having a low atomic number. As shown in the cross section A—A the leads 6, 7 are connected to wires 101, 102 having isolated mantles 103, 104. In a preferred embodiment, the outer diameter of the tubular element is smaller than 2 mm. The cannula is then sufficiently small to penetrate tissue in order to reach a certain location where radiation therapy is required.

FIG. 4 shows a further embodiment where the source 200 is located near the distal end of a wire 201, having high bending flexibility in order to prevent organs and tissue from perforation or penetration by mistake. Instead, the wire 201 can be guided to the tissue where radiation therapy is required by insertion through a catheter which has previously been inserted in the tissue by well-known techniques. A cross section B—B of the wire 201 shows that it consists of a tubular member 202, and power transmitting leads 203, 204. The leads 203, 204 are proximally connectable to an external power source by connecting elements 205, 206. Geometrically, the connecting elements 205, 206 have a diameter approximately equal to the diameter of the wire in order to allow insertion of the wire into a catheter.

Figure 7A:
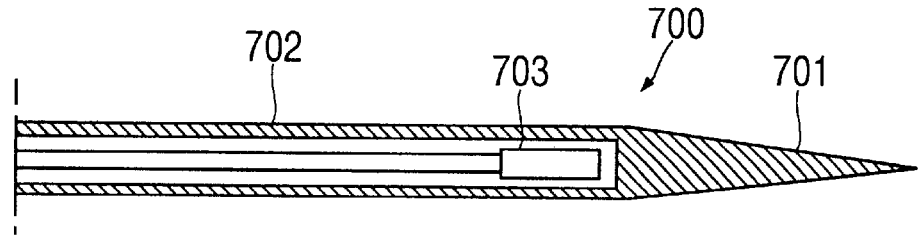
FIG. 7a illustrates an alternative needle structure for accommodating a radiation source.
Figure 7B:
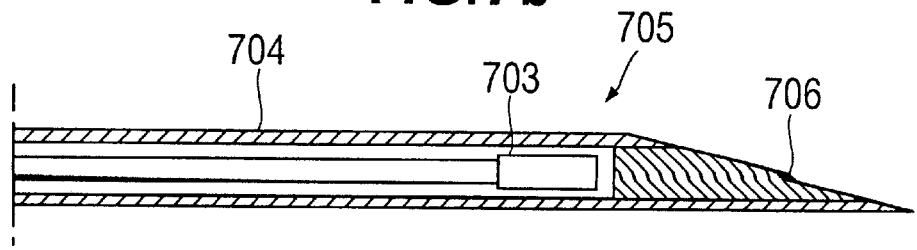
FIG. 7b illustrates a second alternative needle structure for accommodating a radiation source.

Referring now to FIG. 7a and b, other vehicles for the radiation source are conceivable, e.g a needle 700 with a solid distal portion 701 having a sharp tip for the easy penetration of soft and hard tissue, and a hollow portion 702, proximal of the solid tip, wherein the radiation source 703 is mounted. In still another embodiment the radiation source may be mounted in a tube 704, the distal end of which, 705, has been bevelled to render it sharp enough for penetration purposes. The open end of the tube may be plugged at 706 in order that the interior of the tube housing the source not be soiled by tissue.

The power leads supplying power to the radiation source can either be electrical or fiberoptic leads, according to well-known technology. In the case of optical power transmission, it is necessary to convert the optical power into electrical voltage in order to provide voltage supply to the source. This may be done by providing optical energy through the fiberoptic leads and letting the light impinge onto a photodiode which converts the light into a voltage.

Figure 5:
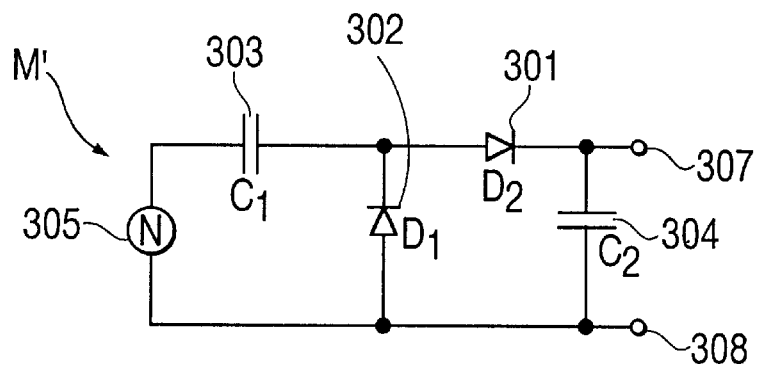
FIG. 5 shows an electronic circuit element, mediating voltage supply to the source.

FIG. 5 shows an electronic circuit element M capable of multiplying an input voltage 305 to its output terminals 307, 308 by a factor of approximately two. The circuit operates with two switching elements, for example diodes 301, 302, and two capacitors 303, 304. If two circuit elements as that shown in FIG. 5 are cascaded, the input voltage will be multiplied by a factor of approximately four. Even larger multiplication factors are possible by cascading more circuit elements of a similar type. The diodes 301, 302 may be replaced by other switching elements, such as transistors.

Figure 8A:
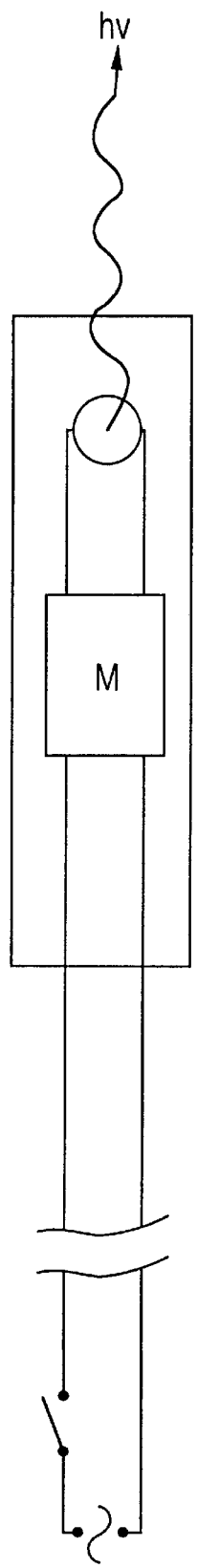
FIG. 8a is a schematic illustration of an integrated voltage multiplying circuit and a radiation source.
Figure 8B:
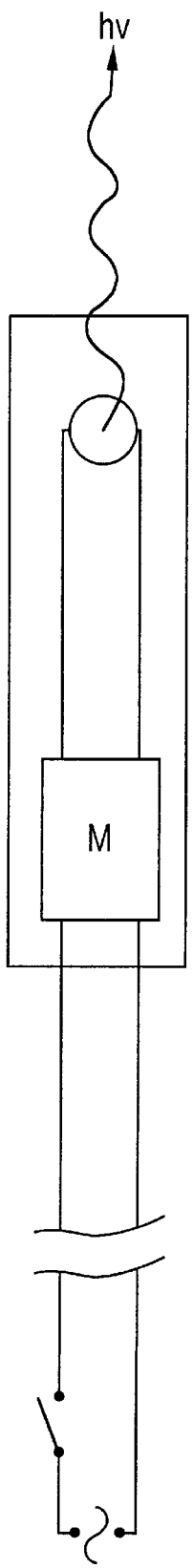
FIG. 8b is a schematic illustration of a voltage multiplying circuit and a radiation source disposed on separate chips adjacent each other.

Preferably, electronic circuitry M such as that shown in FIG. 5 may be integrated with one of the plates 2, 3 accommodating the source (schematically shown in FIG. 8a). Alternatively, the circuitry consists of a separate electronic chip located close to the source (schematically shown it FIG. 8b).

The high voltage generation may of course alternatively be disposed outside the body, e.g in the external power supply.

In a preferred embodiment of the invention, the anode and cathode are designed and disposed as shown in FIG. 9.

As shown, both the anode 91 and the cathode 92 have essentially the shape of a cone (or a pyramid having three of more sides) each having a pointed tip 93, 94, the tips facing each other. The orientation is such that the symmetry axis of the anode and that of the cathode, are parallel with or coincide with the longitudinal axis of the rod or other elongated device 201 in which they are mounted. Because of the mechanism of the field emission effect, namely that the emitted soft X-ray radiation is perpendicular to the angle of incidence of the impinging electrons (electron energy 1–50 keV), by orientating the electrodes in this manner, one obtains a distribution of emitted radiation that is essentially circular, i.e. covers an angle of 360°, thus forming a lobe around the radiation source. Thus, the tissue surrounding the location of the radiation source will be irradiated to essentially the same extent in all lateral directions. The radiation source is enclosed in an X-ray transparent thin tubing or sleeve 95, e.g. of glass or other material capable of transmitting X-rays.

Various conceivable shapes of the electrodes are shown in FIGS. 10 a), b) and c).

In a variation of the embodiment shown in FIG. 9, the electrodes are formed as wedges, the edges of which facing each other, see FIG. 11. FIG. 11 a) shows a side view in cross section of a radiation source, wherein the electrodes, cathode 51, anode 61, are located in a recess 52 in a main body 54, with the ages 56, 66 facing each other. FIG. 11 *b*) is a top view of the device according to this embodiment. A conductor, such as a conducting strip 58 of deposited metal connects the cathode to a voltage source, and a conductor, such as deposited strip 68 connects the anode to said voltage source. The details of how to connect the electrodes are not important, and the skilled man will be able to find a suitable solution without inventive work.

This electrode configuration will produce a distribution of radiation different from that of the configuration of FIG. 9, in that it will be more concentrated towards two opposed sides.

In still a variation of the invention, it is conceivable to use a ferro-electric material for the cathode. The principles behind electron emission from ferro-electric materials are reviewed in "Nuclear Instruments and Methods in Physics Research A", 340 (1994), 80–89.

An advantage of using a ferro-electric material as a cathode, is that it becomes possible to obtain electron self-emission without any external extraction field.

Instead one uses fast polarization switching of the electrodes for generating macroscopic charge separation on two opposite surfaces of a ferro-electric material. The resulting space-charge (polarization) fields are so high that self-emission takes place.

The fast switching of spontaneous polarization necessary for achieving the desired self-emission may be provided in several ways. Methods include temperature changes, electric field HV or mechanical-pressure pulses, and pulsing with laser irradiation.

Single-crystalline or poly-crystalline materials such as ceramics may be used. Examples of suitable materials are Pb-Zr-titanate (PZT), Pb-La-Zr-titanate (PLZT), Ba $TiO_3$, $PbTiO_3$, $LiNbO_3$, $KNO_3$, tri-glycerin-sulphate, but the skilled man would be able to find other suitable materials as desired.

Figure 12:
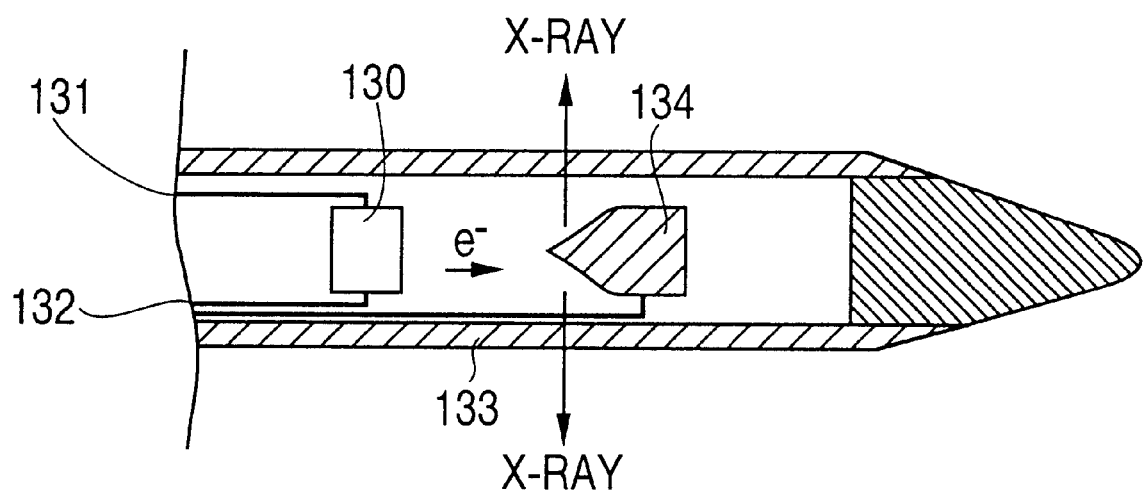
FIG. 12 shows an embodiment of the device according to the invention having a ferro-electric cathode, and means for generating an acceleration field between anode and cathode.

In FIG. 12 there is shown an embodiment of the device according to the invention with a ferro-electric cathode. This embodiment is provided with means for creating an acceleration field between cathode and anode. Thus, there are provided electrical leads 121, 122 connecting the cathode 120 to a power source for providing a pulsed high voltage in order to generated electron emission, and a lead 123 connecting the anode 124 to a high voltage source (not shown). The provision of such acceleration field will enhance the emission.

Figure 13:
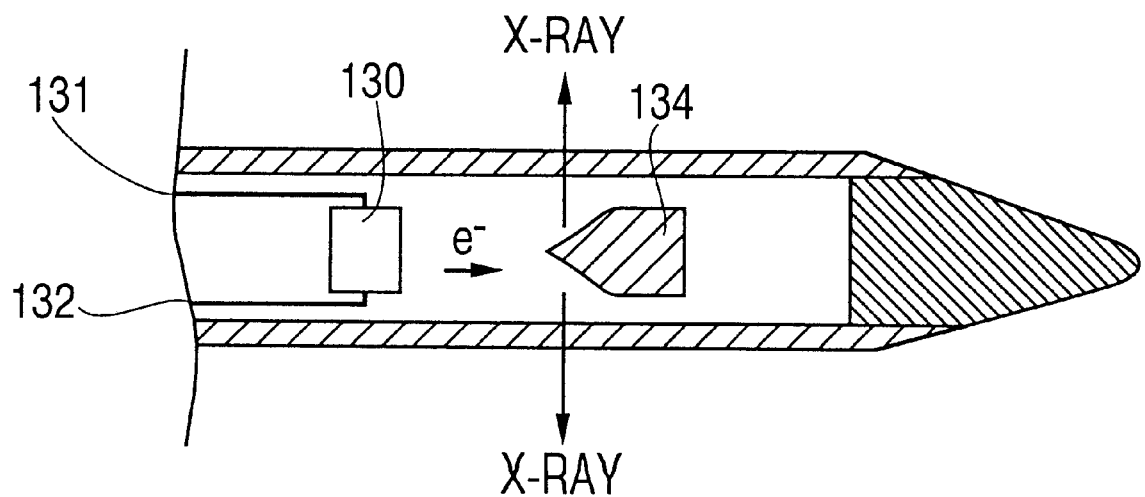
FIG. 13 shows an embodiment of the device according to the invention having a ferro-electric cathode, but without any means for generating an acceleration field between anode and cathode.

However, as shown in FIG. 13, the device will function also without any imposed acceleration field. In this case only the pulse generation power source is necessary, and therefore only the leads 131, 132 are connected to the cathode 130, the anode 134 being electrically isolated from the cathode.

The method of providing a controlled dose of radiation is carried out as follows.

The physician localizes the region of interest, e.g. a tumor to be treated. Depending on the site and type of tissue, various vehicles for the radiation source may be employed, e.g. a needle for penetrating through soft tissue, or a guide wire possibly in combination with a catheter, or the insertion may be made through blood vessels or other body channels, such as intestines. When the radiation source has been correctly located inside the body, the radiation source is activated and the required dose is given. The device is switched off and the source is withdrawn from the patient. This procedure may easily be repeated frequently until the desired clinical result has been achieved.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A miniaturized source of ionizing electromagnetic radiation, comprising:
   a) a pair of plates;
   b) a hermetically sealed microcavity formed in one of the plates;
   c) a pair of electrodes in the form of a cathode and an anode, at least one electrode being located in the microcavity and the other electrode being located on the other plate;
   d) the anode being at least partly of a metal having a relatively high atomic weight; and
   e) electrically conducting leads connected to the cathode and the anode.

2. The miniaturized source according to claim 1, wherein the cavity is formed between the plates and wherein the plates are bonded together.

3. The miniaturized source according to claim 1, wherein a base in the microcavity has the shape of a sharp tip.

4. The miniaturized source according to claim 3, wherein one electrode is formed on the sharp tip.

5. The miniaturized source according to claim 3, wherein the cathode is formed on the sharp tip.

6. The miniaturized source according to claim 3, wherein the sharp tip is directed toward the anode.

7. The miniaturized source according to claim 6, wherein the radius of curvature on the tip is in the nanometer range.

8. The miniaturized source according to claim 1, wherein the microcavity is formed in one of the plates by etching a sacrificial layer in one on the plates.

9. The miniaturized source according to claim 1, wherein the cathode comprises an element having a low work function.

10. The miniaturized source according to claim 9, wherein the cathode is at least partly of a metal selected from a group consisting of cesium, barium, and magnesium.

11. The miniaturized source according to claim 1, wherein at least one of the plates is comprised of a single crystalline silicon.

12. The miniaturized source according to claim 1, further comprising at least one gate electrode having an electrically conducting lead controlling the electron current from the cathode to the anode.

13. The miniaturized source according to claim 1, wherein at least one of the plates is transparent to radiation.

14. The miniaturized source according to claim 1, wherein at least one of the leads is formed as an integral part of at least one of the plates.

15. The miniaturized source according to claim 1, wherein the source is enclosed in a tubular element transparent to radiation, the leads also being enclosed in the tubular element.

16. The miniaturized source according to claim 1, including at least one passivating layer between the leads, providing isolation therebetween.

17. The miniaturized source according to claim 1, wherein the source is at the distal portion of a wire, the distal portion possessing high bending flexibility.

18. The miniaturized source according to claim 17, wherein the source and leads are enclosed within a tubular member.

19. The miniaturized source according to claim 1, including a voltage supply connectable to the leads, the supply comprising a plurality of switching capacitive elements configured to multiply the input voltage by a predetermined factor at the leads.

20. The apparatus of claim 1, wherein the cathode and/or the anode have the shape of a cone, or a pyramid with at least three side surfaces.

21. The apparatus of claim 20, wherein the cathode and the anode are arranged such that their apexes point towards each other.

22. The apparatus of claim 21, wherein the cathode and the anode are arraigned such that their axis of rotation are parallel with or coincide with the longitudinal axis of said elongated member.

23. The apparatus of claim 1, wherein the cathode and the anode have the shape of a wedge, the pointed edges of which face each other.

24. The apparatus of claim 23, wherein the cathode and the anode are arranged such that their apexes point towards each other.

25. The apparatus of claim 23, wherein the cathode and the anode are arranged such that their axis of rotation are parallel with or coincide with the longitudinal axis of said elongated member.

26. The apparatus of claim 1, wherein the cathode is made of a ferro-electric material.

27. The apparatus of claim 25, comprising means for creating a space charge polarization field in the cathode.

28. The apparatus of claim 27, wherein said space charge polarization field creating means include any of means for generating heat pulses, means for inducing mechanical pressure pulses, means for generating high voltage electric field pulses, and means for generating laser pulses.

29. The apparatus of claim 28, comprising means for creating an acceleration field between cathode and anode.

30. The apparatus of claim 1, wherein the anode comprises a base matrix (5), and a plurality of micro tips (5') extending from said base matrix.

31. The apparatus of claim 30, wherein said micro tips (5') comprise diamond or a diamond like material, optionally coated with a conductive material.

32. The apparatus of claim 30, wherein said micro tips (5') are provided by making the anode (5) of, or coating it with a material having a surface roughness.

* * * * *